(12) United States Patent
Clark et al.

(10) Patent No.: US 11,134,867 B2
(45) Date of Patent: Oct. 5, 2021

(54) METHOD FOR ACCURATELY ESTIMATING A PURE TONE THRESHOLD USING AN UNREFERENCED AUDIO-SYSTEM

(71) Applicant: Mimi Hearing Technologies GmbH, Berlin (DE)

(72) Inventors: Nicholas R. Clark, Royston (GB); Vinzenz H. Schönfelder, Berlin (DE)

(73) Assignee: Mimi Hearing Technologies GmbH, Berlin (DE)

( * ) Notice: Subject to any disclaimer, the term of this patent is extended or adjusted under 35 U.S.C. 154(b) by 109 days.

(21) Appl. No.: 16/080,785

(22) PCT Filed: Oct. 19, 2017

(86) PCT No.: PCT/EP2017/076679
§ 371 (c)(1),
(2) Date: Aug. 29, 2018

(87) PCT Pub. No.: WO2018/073333
PCT Pub. Date: Apr. 26, 2018

(65) Prior Publication Data
US 2019/0231232 A1 Aug. 1, 2019

(30) Foreign Application Priority Data

Oct. 19, 2016 (EP) ..................... 16194694
Mar. 22, 2017 (EP) ..................... 17162448
May 16, 2017 (EP) ..................... 17171413

(51) Int. Cl.
*A61B 5/12* (2006.01)
*A61B 5/00* (2006.01)

(52) U.S. Cl.
CPC .............. *A61B 5/121* (2013.01); *A61B 5/123* (2013.01); *A61B 5/7267* (2013.01);
(Continued)

(58) Field of Classification Search
None
See application file for complete search history.

(56) References Cited

U.S. PATENT DOCUMENTS 3,784,750 A * 1/1974 Stearns .................... H03G 9/02
  381/320
3,989,904 A * 11/1976 Rohrer ................... A61B 5/121
  381/320

(Continued)

FOREIGN PATENT DOCUMENTS

| EP | 3311741 A1 | 4/2018 |
| WO | 2018073333 A1 | 4/2018 |

OTHER PUBLICATIONS

International Search Report and Written Opinion; PCT Application No. PCT/EP2017/076679; dated Aug. 12, 2017.
(Continued)

*Primary Examiner* — Sean P Dougherty
*Assistant Examiner* — Benjamin S Melhus
(74) *Attorney, Agent, or Firm* — Polsinelli PC

(57) ABSTRACT

Method for estimating a pure tone hearing threshold or a pure tone audiogram of a person with a non-calibrated audio-system, comprising the steps of performing a supra-threshold test at least over a portion of the audible frequency spectrum, wherein the audible frequency spectrum ranges particularly from 16 Hz to 20.000 Hz, wherein the supra-threshold test is performed on an unreferenced audio-system at a first relative sound level relative to a predefined output level of the unreferenced audio-system, determining the result of the supra-threshold test for at least a portion of the audible frequency spectrum, wherein the results of the supra-threshold test are provided particularly relative to the predefined output level of the unreferenced audio-system, determining from the progression of the determined result of the supra-threshold test at least one absolute pure tone
(Continued)

threshold, wherein the at least one absolute pure tone threshold is provided in absolute physical units, particularly in decibels hearing level or decibels sound pressure level.

14 Claims, 6 Drawing Sheets

(52) U.S. Cl.
    CPC .......... *A61B 5/7278* (2013.01); *A61B 5/7415* (2013.01); *A61B 2560/0223* (2013.01)

(56) References Cited

U.S. PATENT DOCUMENTS

| | | | |
|---|---|---|---|
| 4,060,701 A | 11/1977 | Epley | |
| 5,785,661 A | 7/1998 | Shennib | |
| 2001/0049480 A1* | 12/2001 | John | A61B 5/121 600/559 |
| 2002/0091423 A1* | 7/2002 | Rubinstein | H04R 25/75 607/55 |
| 2004/0064066 A1* | 4/2004 | John | A61B 5/04845 600/559 |
| 2012/0029383 A1 | 2/2012 | Henriksen et al. | |
| 2013/0274628 A1* | 10/2013 | Fausti | A61B 5/123 600/559 |
| 2014/0309549 A1* | 10/2014 | Selig | A61B 5/123 600/559 |
| 2015/0222999 A1* | 8/2015 | Rasmussen | 381/60 |
| 2015/0350794 A1* | 12/2015 | Pontoppidan | H04R 25/00 381/321 |
| 2015/0358745 A1* | 12/2015 | Rix | H04R 25/305 381/60 |
| 2017/0265786 A1* | 9/2017 | Fereczkowski | A61B 5/123 |

OTHER PUBLICATIONS

Morgan, Donald E et al., "Influence of middle-ear muscle contraction on pure-tone suprathreshold loudness judgments", The Journal of HTE Acoustical Society of America; vol. 57, No. 2; Feb. 1, 1975.
British Society of Audiology (BSA); "Guidelines for Pure Tone Air Conduction Audiometry Silent Surrounding"; http://www.thebsa.org.uk/wp-content/uploads/2014/04/BSA_RP_PTA_FINAL_24Sept11_MinorAmend06Feb12.pdf.
Carney, A. E., & Nelson, D. A; (1983) "An analysis of psychophysical tuning curves in normal and pathological ears"; The Journal of the Acoustical Society of America, 73(1), 268-278.
Florentine, M., Buus, S., Scharf, B., & Zwicker, E.; (1980); "Frequency Selectivity in Normally-Hearing and Hearing-Impaired Observers"; Journal of Speech Language and Hearing Research, 23(3), 646-24.
Hopkins, K., & Moore, B. C. J.; (2007) "Moderate cochlear hearing loss leads to a reduced ability to use temporal fine structure information"; The Journal of the Acoustical Society of America, 122(2), 1055-1068.
Hopkins, K., & Moore, B. C. J.; (2011); "The effects of age and cochlear hearing loss on temporal fine structure sensitivity, frequency selectivity, and speech reception in noise"; The Journal of the Acoustical Society of America, 130(1), 334-349.
Moore, B. C. J., Vickers, D. A., Plack, C. J., & Oxenham, A. J. (1999). Inter-relationship between different psychoacoustic measures assumed to be related to the cochlear active mechanism. The Journal of the Acoustical Society of America, 106(5), 2761-2778.

* cited by examiner

METHOD FOR ACCURATELY ESTIMATING A PURE TONE THRESHOLD USING AN UNREFERENCED AUDIO-SYSTEM

CROSS-REFERENCE TO RELATED APPLICATIONS

This application is a national stage application of International Application No. PCT/EP2017/076679, which was filed on Oct. 19, 2017, which claims priority to European Application Number 17171413.2 filed on May 16, 2017, European Application Number 17162448.9 filed on Mar. 22, 2017, and European Application Number 16194694.2 filed on Oct. 19, 2016, each of which are incorporated by reference in their entireties.

TECHNICAL FIELD

The invention relates to a method and a computer program for estimating a pure tone audiogram from data acquired on an unreferenced or non-calibrated audio-system.

BACKGROUND

Hearing tests are usually performed under controlled conditions. Particularly pure tone threshold tests that estimate an audiogram comprising the hearing threshold (i.e. the lowest sound intensity a person can detect) of a person for a plurality of frequencies are to be performed using a well-defined audio-system. These tests are usually performed in a controlled noise environment, such as for example defined in the British Society of Audiology (BSA) guidelines for pure tone air conduction audiometry silent surrounding so that no external noise interferes with the signals provided to the test person. The BSA guidelines are for example accessible via the link below and known to the person skilled in the art:

http://www.thebsa.org.uk/wp-content/uploads/2014/04/BSA_RP_PTA_FINAL_24Sep.11_MinorAmend06Feb12.pdf More importantly, the audio-system that comprises for example the headphone and the signal generator have to provide sounds with known audio-characteristics to the person in order to be able to determine the pure tone threshold in absolute physical units of audio or sound level, such as decibel sound pressure level. Otherwise these audiograms would not be comparable to other audiograms and thus, e.g. diagnosing and quantifying a hearing loss would not be possible.

Hearing test results are particularly also given in decibel hearing level (dB HL), which is similar to decibel sound pressure level (dB SPL), but normalised to a standardised curve of normal hearing across frequency rather than a fixed reference of 20 micro Pascal. The person skilled in the art is able to convert from dB HL to dB SPL. For the above-mentioned reason, the audio-systems for performing hearing tests are usually calibrated, so that a quantitative audiogram can be acquired.

It is not possible to accurately determine a pure tone threshold from a non-calibrated audio-system or an audio-system that lacks a referenced output-level, i.e. the audio-system is unreferenced and the output audio-level of such a system is not known in absolute physical units, such as sound pressure, sound energy or intensity.

Unreferenced audio-systems are for example off-the-shelf smart-phones with some kind of off-the-shelf headphone.

Thus, an unreferenced audio-system is particularly any audio-system from which the output level with respect to a certain frequency is not known in absolute physical units, such as for example decibel sound pressure level, or decibel hearing level. However in the context of the specification an unreferenced audio-system is assumed to provide a sufficiently flat output characteristic with regard to a sound level for a specific frequency.

The term "sufficiently flat" particularly refers to a frequency response of the audio-system, particularly the headphones, that is within a 10 dB, particularly 15 dB, deviation of the expected sound level across the range of 250 Hz to 8000 Hz.

The terms "unreferenced" and "uncalibrated" are used synonymously in the description.

In contrast to threshold measurements, so called supra-threshold tests are focusing on other aspects of a person's hearing ability and by definition rely on stimuli presented above the hearing threshold of a person.

For example, the psychometric tuning curve (PTC) is one such measure that estimates the frequency resolution of the auditory perception.

Also the temporal fine structure (TFS) test is a supra-threshold test, wherein the TFS test estimates the ability of the inner hair cells (units responsible for converting mechanical vibrations in the cochlear to neural spiking code) to resolve the rapid oscillations in a modulating signal in the absence of spectral cues.

The result of the TFS test for each frequency region of interest is a frequency discrimination threshold in Hz. So unlike the results of the PTC test, which can typically be displayed as a v-shaped plot around each frequency region under test, the results of a TFS test only return a single value for each frequency region under test, i.e., it is not as data rich as the results form a PTC test.

The level of supra-threshold stimuli is often defined in terms of decibel sensation level (dB SL) (relative to the individual hearing level) and at least to some extent the measurement result often does not depend on the absolute physical sound level of the stimuli.

The problem underlying the present invention is to provide a method and a computer program allowing the determination of at least one pure tone threshold or a whole pure tone audiogram, with or on an unreferenced audio-system.

PRIOR ART

Florentine, M.. Buus. S., Scharf, B., &-Zwicker, E. Frequency Selectivity in Normally-Hearing and Hearing-Impaired Observers, Journal of Speech Language and Hearing Research, 23(3), 646-24. httD://doi.org/10.1044/ishr.2303.646

Carney, A. E., & Nelson, D. A. (1983). An analysis of psychophysical tuning curves in normal and pathological ears. The Journal of the Acoustical Society of America, 73(1), 268-278. http://doi.ora/10.1121/1.388860

Moore, B, C, J., Vickers, D. A., Plack, C, J., & Oxenham, A. J. (1999). Inter-relationship between different psycho-acoustic measures assumed to be related to the cochlear active mechanism. The Journal of the Acoustical Society of America, 106(5), 2761-2778. http://doi.orq/10.1121/1.428133

Hopkins. K.. & Moore. B. C. J. (2007), Moderate cochlear hearing lossJ leads to a reduced ability to use temporal fine structure information. The Journal of the Acoustical Society of America, 122(2), 1055-1068, http://doi.oro/10.1121/1.2749457

Hopkins. K., & Moore, B, C. J. (2011). The effects of age and cochlear hearing loss on temporal fine structure sensitivity, frequency selectivity, and speech reception, in noise. The Journal of the Acoustical Society of America, 130(1), 334-349, http://doi.orq/10.1121/1.3585848

BRIEF DESCRIPTION OF THE DRAWINGS

In order to describe the manner in which the above-recited and other advantages and features of the disclosure can be obtained, a more particular description of the principles briefly described above will be rendered bv reference to specific embodiments thereof which are illustrated in the appended drawings. Understanding that these drawings depict only exemplary embodiments of the disclosure and are not therefore to be considered limiting of its scope, principles herein are described and explained with additional specificity and detail through the use of the accompanying drawings in which.

Description of Example Embodiments

Figure 1:
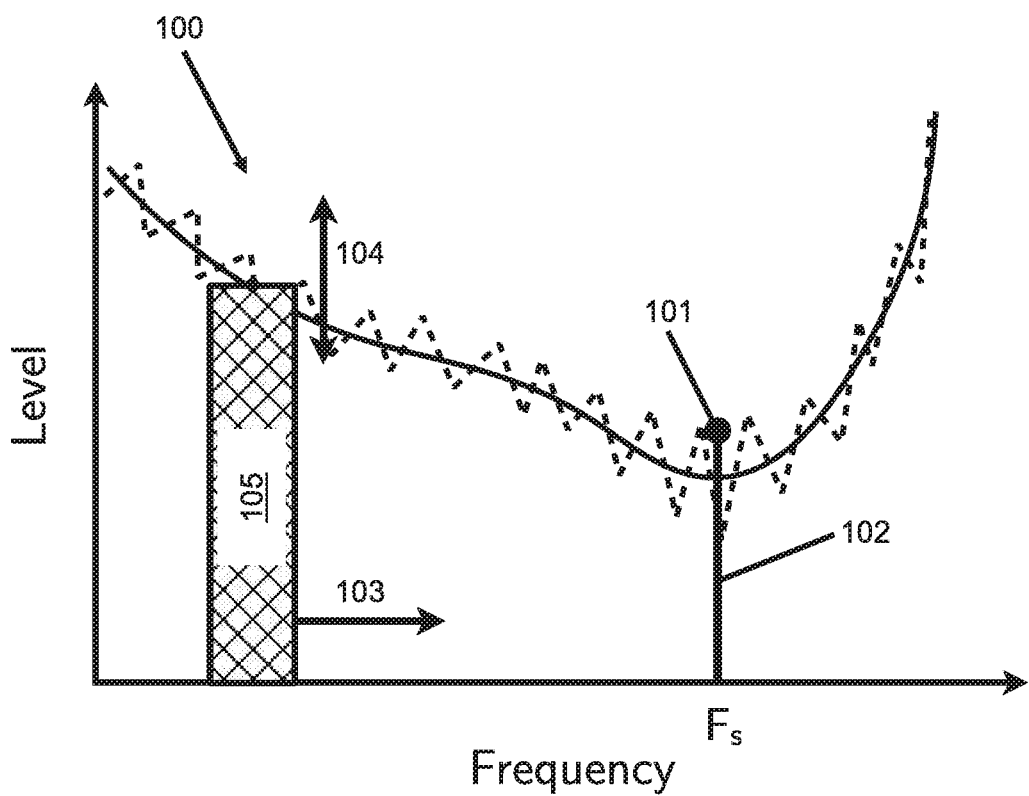
FIG. 1 shows an illustration of a PTC measurement, according to one aspect of the present disclosure.

According to claim 1, a method for estimating a pure tone hearing threshold or a pure tone audiogram of a person with a non-calibrated audio-system, comprises the steps of:

performing a supra-threshold test at least over a portion of the audible frequency spectrum with a person, wherein the audible frequency spectrum ranges particularly from 16 Hz to 20,000 Hz, wherein the supra-threshold test is performed on an unreferenced audio-system at a first sound level relative to a predefined output level of the unreferenced audio-system, particularly wherein the first sound level is above the hearing threshold of the person, where particularly comfortable hearing is possible, particularly 20 decibels to 50 decibels above a pure tone threshold, determining the result of the supra-threshold test for at least a portion of the audible frequency spectrum, wherein the result of the supra-threshold test is provided particularly relative to the predefined output level of the unreferenced audio-system, determining from the result of the supra-threshold test at least one absolute pure tone threshold particularly for at least one frequency, wherein the at least one absolute pure tone threshold is provided in absolute physical units, particularly in decibels hearing level or in decibels sound pressure level.

An alternative solution to the problem according to the invention is given by a method for accurately estimating a pure tone hearing threshold or a pure tone audiogram of a person with a non-calibrated or unreferenced audio-system, comprises the steps of:

particularly performing a hearing threshold estimation in arbitrary units on an unreferenced audio-system, performing a supra-threshold test at least over a portion of the audible frequency spectrum, wherein the audible frequency spectrum ranges particularly from 16 Hz to 20,000 Hz, wherein the supra-threshold test is performed on an unreferenced audio-system at a first sound level particularly relative to a predefined output level of the unreferenced audio-system, determining the result of the supra-threshold test for at least a portion of the audible frequency spectrum, wherein the results of the supra-threshold test are provided relative to the predefined output level of the unreferenced audio-system, determining from result of the supra-threshold test, particularly the progression, or shape or specific features of the determined result, at least one absolute pure tone threshold for at least one frequency, wherein the at least one absolute pure tone threshold is provided in absolute physical units, particularly in decibels hearing level or in decibels sound pressure level.

According to another embodiment of the invention, the first particularly relative sound level is above the hearing threshold of the person, where particularly comfortable hearing is possible.

The term "comfortable" in the context of the specification is particularly defined as where signal, or probe stimulus components are clearly audible without being uncomfortably intense. Simultaneously, any masking stimulus components used in the supra-threshold test (STT) paradigms can effectively mask the signal without needing to be presented at an uncomfortable intensity that is particularly below 90 dB SPL.

The determination of the pure tone threshold is facilitated by particularly analysing the shape, the progression or other features of the supra-threshold test result and conclude on an absolute value of the pure tone threshold.

The result of the supra-threshold test is particularly a series of value or value pairs that can be represented as a plot. Likewise, the result of the supra-threshold test can comprise characterizing or descriptive parameters that are the result from a first evaluation of the supra-threshold test and that are configured to reduce the amount of information on the supra-threshold test. Said parameters can serve for the determination of the at least one absolute pure tone threshold.

In case the supra-threshold result is represented as a plot of values or value pairs, said plot particularly exhibits a shape, a progression or shape-specific features that can be evaluated for concluding on the pure tone threshold.

The relation between the supra-threshold test result and the at least one absolute pure tone threshold might not be exactly known, but it can be modelled for example by means of a multivariate analysis, or a particularly supervised learning algorithm. Furthermore, artificial neuronal networks, methods comprising a support vector machine with trained classifiers, for classifying an obtained result from the supra-threshold test to a corresponding absolute the pure tone threshold are suitable as well.

According to one embodiment of the invention, in a first optional step, a comfortable hearing level is determined for example by estimating a pure tone threshold, wherein the pure tone threshold can be expressed particularly only relative to a predefined output level, for example relative to the to the maximum output level (e.g. volume at 100%) of the audio-system.

In case a pure tone threshold test is performed on the unreferenced audio-system prior the supra-threshold test, it is possible, to determine a comfortable hearing level, for example by adjusting the first sound level of the audio-system for example 20 dB higher than the estimated pure tone threshold.

Alternatively the first sound level can be adjusted to 50%, 30% or any suitable fraction of the maximum output level of the unreferenced audio-system.

Subsequently the supra-threshold test is presented at said comfortable first sound level, wherein the absolute physical units of the supra-threshold test result are of no particularly concern.

As long as the units are in decibels relative to each other, the supra-threshold test result can be evaluated for example in terms of its shape (of the plot of the values or pairs). This holds particularly true in case the supra-threshold test is a psychometric tuning curve (PTC) test.

In case the supra-threshold test is a temporal fine structure (TFS) test, the resulting units are in Hz, so relative or absolute level is not applying to this test.

It is furthermore noted that in the TFS test, two alternating sounds are presented, these can be in the region of about 20-80 dB HL. In the PTC test, the probe tone is presented at about 20-50 dB HL, but the masker tone used in the test can be at much higher level as it needs to mask the probe. The masker tone can be up to about 90 dB HL. This is why the probe should be at quite a low level of presentation, i.e. particularly at the comfortable hearing level.

The first sound level at which the supra-threshold test is conducted, therefore particularly refers to the probe tone in case of a PTC test and to the alternating sounds that are presented during a TFS test.

The invention takes advantage of the finding that a supra-threshold test result, particularly the shape of a PTC test does not depend—within certain limits—on the provided audio level, particularly the first sound level, i.e. there is a certain amount of level invariance for a given user.

Therefore, as long as the provided signal is (a) above the hearing threshold and (b) not excessively above hearing threshold, deviations in the supra-threshold test result from another supra-threshold test result corresponding to normal hearing abilities can be assigned to interpersonal hearing differences, which allows making the predictions about the absolute pure tone thresholds.

Therefore, by carefully analysing the supra-threshold test result, particularly the shape and the features of the supra-threshold test result, it is possible to conclude on the at least one absolute pure tone threshold.

The estimate becomes particularly better when a second potentially different supra-threshold test is performed. The term "different" refers particularly to a different kind of supra-threshold test and/or to a supra-threshold test performed at a different sound level and/or a different frequency.

Also, the method according to the invention performs particularly more reliable when only sensorineural hearing losses are considered, when determining the at least one pure tone threshold.

It is particularly one goal of the invention to determine a plurality of pure tone thresholds for different frequencies such that at least a portion of an audiogram of the person can be established.

The method according to the invention is advantageously providing a cost-effective tool to perform pure tone threshold estimation on "every day" devices such as smartphones, computers and the like, which in turn can be used to adjust the device's output characteristic for an enhanced hearing experience of the person.

A supra-threshold test is performed at a sound level that is recognized (i.e. above the hearing threshold) by the person, as the sounds provided to the person are within the persons hearing range.

As the output level of the unreferenced audio-system is not known in absolute values, such as decibel sound pressure, a first sound level that is adjusted relative to a predefined output level of the audio-system is chosen to perform the supra-threshold test. The predefined output level of the audio-system can be for example the maximum output level or a fraction of the maximum output level of the audio-system, such that the first sound level can be expressed and referred relative to said predefined output level.

According to another embodiment of the invention, a supra-threshold test result comprises or is a set of characterizing parameters, wherein the characterizing parameter set comprises at least one parameter, wherein said parameter is configured to describe a progression, a shape feature, a gradient and/or a shape of the particularly graphical representation of the supra-threshold test result or wherein said characterizing parameter set is or comprises principal components of the supra-threshold test result, wherein the characterizing parameter set particularly comprises not more than 5 principal components of the supra-threshold test result.

As mentioned above, the characterizing parameter set helps to reduce the amount of information from the supra-threshold test result, such that file sizes comprising the results can be reduced. Furthermore, various mathematical concepts can be applied to the characterizing parameter set that are not suitable for "raw" data from the supra-threshold test result e.g. the measured tuning curves.

According to another embodiment of the invention, the at least one absolute pure tone threshold is determined by a regression function, wherein the supra-threshold test result, particularly in form of a characterizing parameter set, of the performed supra-threshold test is submitted to said regression function, wherein said regression function is configured to determine from the submitted supra-threshold test result the at least one pure tone threshold.

Determining the at least one pure tone threshold by means of a regression function has particularly the advantage that a particularly continuous function can be used for determining the absolute pure tone threshold. The regression function can be refined at any time with a more suitable regression relation or more suitable regression coefficients.

The regression function can be a parametric regression function or a semi-parametric regression function. The regression function does not have to be linear.

According to another embodiment of the invention, the regression function is determined by the steps of:

Providing a training set comprising a plurality of supra-threshold test results, each particularly in form of a characterizing parameter set, wherein said supra-threshold test results are particularly estimated from a plurality of people, wherein to each supra-threshold test result of the training set, at least one pure tone threshold is associated, Determining from the training set a regression function between the supra-threshold test results and the associated at least one pure tone threshold by means of a regression analysis.

The provision of training data is particularly advantageous for estimating a functional connection between supra-threshold test results and corresponding absolute pure tone thresholds.

The training set particularly comprises supra-threshold test results and/or characterizing parameter sets from different people, particularly exhibiting different hearing abilities resulting in different absolute pure tone thresholds.

The differences in the characterizing parameter set or in the shape, progression or other features of the supra-threshold test results are cues that can be evaluated and that basically code for a uniquely assignable absolute pure tone threshold.

According to another embodiment of the invention, the regression function is a multivariate linear regression function, wherein particularly the variables of the regression function for submitting the characterizing parameters, and particularly wherein the coefficients for the regression function have been determined from a training set; particularly from the training set.

The multivariate linear regression function is found to model the relation between supra-threshold test result and the at least one absolute pure tone threshold sufficiently accurate for being used to predict or determine the at least one absolute pure tone threshold.

According to another embodiment of the invention, more absolute pure tones thresholds than the at least one pure tone threshold are determined, wherein each of the absolute pure tone thresholds is determined for a different frequency, wherein particularly a whole pure tone threshold audiogram, particularly comprising six absolute pure tone thresholds at different frequencies, is determined.

Pure tone thresholds can be estimated throughout the audible frequency spectrum, wherein it has to be taken care of the audio-system's hardware, as many speakers have cut-off frequencies that are within the audible range. To obtain an audiogram, usually several, particularly 5 to 10, pure tone threshold suffice.

Alternatively or additionally to the regression function approach, it is also possible to choose a look-up table approach, where supra-threshold test results are compared to each other. Similar supra-threshold test results will be assigned similar absolute pure tone thresholds. The similarity between two supra-threshold test results can be estimated by a specific similarity metric.

According to another embodiment of the invention, the at least one absolute pure tone threshold is determined by the steps of:
 Providing a database of a plurality of supra-threshold test results, particularly acquired from a plurality of persons, wherein at least one absolute pure tone threshold or an absolute pure tone audiogram is associated to each provided supra-threshold test result of the plurality of supra-threshold test results,
 Determining a similar supra-threshold test result from the database particularly by means of a predefined similarity or distance metric between the supra-threshold test results, wherein the similar supra-threshold test result is the most similar supra-threshold test result of the similarity metric to the supra-threshold test result from the performed supra-threshold test,
 Assigning the at least one absolute pure tone threshold associated to the similar supra-threshold test result to the supra-threshold test result from the performed supra-threshold test.

A similarity metric can be for example established by state of the art chi-square estimators or other robust estimators. Also, a correlation coefficient or another correlation based method can be used to determine a similarity between two supra-threshold test results.

In case the supra-threshold test result from the performed supra-threshold test is similar to a plurality of supra-threshold test results from the database, it is also possible to combine the associated absolute pure tone thresholds to a single, particularly weighted, pure tone threshold.

According to another embodiment of the invention, the similarity metric between two supra-threshold test results is designed to evaluate a similarity, wherein the similarity metric particularly is or comprises a difference, an absolute value of the difference, a chi square estimator, a residual, a correlation coefficient, a linear regression method, or a machine learning method, particularly a trained classifier.

According to another embodiment of the invention, the supra-threshold test comprises or is a psychometric tuning curve test (PTC) and/or comprises or is a temporal fine structure test (TFS), and/or comprises or is a temporal masking curve test.

Particularly if the supra-threshold test is a TFS test, it is possible to correlate the result of said test at a particular frequency with a known database of TFS test result data, as described in the above mentioned embodiment.

It is however also possible to perform a TFS test and a PTC test, and evaluate both tests and compare the respective determined at least one absolute pure tone thresholds, particularly in order to cross-check the results. Also, it is possible to combine, e.g. average, the determined at least one absolute pure tone threshold of the two tests (TFS and PTC). Furthermore, if there is a discrepancy from an expected norm, e.g. showing a pathological deviation from a normal hearing ability, it is possible to disregard the determined pure tone threshold, or re-test or analyse the discrepancy in terms of a more specific form of hearing loss.

According to another embodiment of the invention, a plurality of supra-threshold tests is performed on the unreferenced audio-system, wherein the supra-threshold tests are particularly performed at different sound levels and/or in different portions of the frequency spectrum.

The determination of the at least one pure tone threshold becomes more reliable, and stable, when a plurality of supra-threshold tests are performed and evaluated.

According to another embodiment of the invention, the supra-threshold test is a psychometric tuning curve test (PTC), wherein the PTC is particularly measured for signal tones at frequencies of 500 Hz, 1 kHz, 2 kHz and/or 4 kHz, and particularly at a signal level of 20 dB SL, 30 dB SL, and/or 40 dB SL, or at signal levels between these signal levels, wherein particularly a masking signal for each signal tone sweeps in a predefined range around the signal tone frequency, particularly from 60% of the signal tone frequency to 140% of the signal tone frequency.

According to another embodiment of the invention the signal level of the masker, i.e. signal level of the masking signal, is particularly continually modulated according to a user responses to the tone. Particularly if the user responds that they can detect the signal tone, the masker signal level is increased, and if the user indicates they cannot detect the signal tone, the masker signal level is decreased.

In a calibrated system, more reliable data con be obtained by modulating the masker intensity (i.e. the signal level of the masking signal) around a curve that would provide a constant output in dB HL. This is so that the user does not experience any jumps in intensity due to the nonlinearities of the frequency response hardware setup, or due to differences in human sensitivity to tones of different frequency.

In an uncalibrated audio system however (assuming the output of the audio system is reasonably flat across frequency and particularly given that the precise output level at each frequency is unknown in an uncalibrated system as explained above), the following embodiment is advantageous.

According to this embodiment of the invention, the masker intensity is modulated relative to a standard weighting curve, such as for example A-weighting, such as defined in IEC 61672:2003, or an equal loudness contour, such as defined in ISO226.

This advantageously provides a consistent feel of control of the masker intensity to the user across the frequency range of the test and yields more consistent results.

Another aspect of the invention and another embodiment of the invention relates to a method for accurate pure tone threshold determination.

According to this method, a pure tone threshold or a plurality of pure tone thresholds is estimated by performing the steps of: sweeping a signal tone across frequency and wherein the intensity of the signal tone is modulated according to a user response wherein, when or if the user indicates they can detect the signal tone, the signal tone is reduced in intensity, and when or if the user indicates they cannot detect the signal tone, the intensity of the signal tone is increased.

According to another embodiment of the invention, the decreasing and/or increasing of the signal tone is modulated around or according to a standardised weighting curve or an equal loudness contour.

According to a preferred embodiment of the invention, before the supra-threshold test is performed the following steps are performed:
Performing a pure tone threshold test with the person with the unreferenced audio-system, wherein the provided sound level of the provided frequencies is determined relative to a predefined output level, particularly the maximum level of the unreferenced audio-system,
Determining relative pure tone thresholds, particularly a relative pure tone audiogram comprising the relative pure tone thresholds, from the pure tone threshold test, wherein the relative pure tone thresholds are expressed relative to the predefined output level of the unreferenced audio-system, wherein for the estimation of the at least one absolute pure tone threshold for at least one frequency the relative pure tone thresholds are used.

There are many ways to perform a pure tone threshold test (PTT), but independent on which PTT is used, it is important that the pure tone thresholds can be expressed relative to the predefined output level of the audio-system.

It is particularly assumed that the output of the audio-system is essentially flat across frequency. Alternatively, standardised sensitivity curves across frequency can be employed to generate absolute units. For the rest of the audiometric thresholds a confident estimate of one or more thresholds is known.

For example, the at least one relative pure tone threshold or the whole relative pure tone threshold audiogram can be used
a) for determining the hearing threshold for the subsequent supra-threshold test and thus it can be used to provide a stimulus that is within the comfortable hearing range of the person,
b) for estimating a whole absolute audiogram from the at least one absolute pure tone threshold, as the shape of the relative audiogram from the pure tone threshold test can be used for estimating missing absolute pure tone thresholds for the absolute audiogram, for example by adjusting the scale of the relative values from the audiogram to the absolute value of the at least one pure tone threshold.

According to another embodiment of the invention, the first audio level of the supra-threshold test is higher by a predefined value than at least one of the plurality of relative pure tone thresholds.

According to another embodiment of the invention, the predefined output level is estimated by providing information about the hardware features or components of the audio-system to the method according to the invention, particularly prior the supra-threshold test or prior the pure tone threshold test.

As many manufactures provide some information about their products in terms of output level or other characteristics, this information can be used to generate a better estimate of the absolute output level of the audio-system.

According to another embodiment of the invention, the first sound level is adjustable by the person.

According to another embodiment of the invention, the result from a previous hearing test is provided to the method according to the invention and wherein the results from the hearing test are taken into account when estimating the at least one absolute pure tone threshold.

This helps advantageously to improve the estimation quality of the method with regard to the pure tone threshold.

According to another embodiment of the invention, a plurality of supra-threshold tests are performed and from the results and/or the progression of the results from the plurality of supra-threshold tests the at least one absolute pure tone threshold is determined.

According to another embodiment of the invention, a plurality of supra-threshold test results particularly acquired from a plurality of persons is provided, wherein to each provided supra-threshold test result of the plurality of supra-threshold test results a set of absolute pure tone thresholds or an absolute pure tone audiogram is associated, wherein the at least one absolute pure tone threshold is determined from the set of the pure tone thresholds that is associated to the supra-threshold test results of the plurality of the supra-threshold test results whose progression is most similar to the determined supra-threshold test result from the performed supra-threshold test.

According to another embodiment of the invention, the determined supra-threshold test result is a function of the hearing ability, particularly measured in decibels sound pressure level, and at least one provided frequency, wherein the progression of the supra-threshold test result is particularly a shape, a slope or a specific feature of said function, such as a width of a locally v-shaped or locally parabolic-shaped function progression, a local minimum, and/or the steepness of a locally v-shaped or locally parabolic-shaped function progression.

The hearing ability of a person is particularly described by a function that relates the deviation of the person's hearing ability form a norm population. The hearing ability is form example evaluated by the pure tone thresholds or audiograms.

According to another embodiment of the invention, a plurality of different supra-threshold tests is performed and for each or the combination of them at least one absolute pure tone threshold is determined.

According to another embodiment of the invention, the at least one absolute pure tone threshold is determined in combination with results that have been determined by the method according to the invention, but on a different unreferenced audio-system.

According to another embodiment of the invention, the sound level and/or sound characteristics, such as the frequency distribution of the surroundings of the audio-system is determined prior to performing the supra-threshold test or the pure tone threshold test, and wherein the determined audio level and/or the sound characteristics are taken into account when determining the at least one absolute pure tone threshold.

The problem according to the invention is also solved by a computer program comprising computer program code, wherein the computer program performs the method according the invention, when the computer program is loaded, streamed or executed on the computer.

The terms 'processor' or 'computer', or system thereof, are used herein as ordinary context of the art, such as a general purpose processor or a micro-processor, RISC processor, or DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

A mobile device in the context of this specification is a small computer, particularly small enough to hold and operate in the hand and having an operating system capable of running mobile apps—software applications designed to run on mobile devices. A mobile device is therefore a computerized device that is portable and weights particularly less than 500 g.

A mobile device, such as a mobile phone, a smart phone, a smart watch, a portable music player or a tablet computer, particularly comprises at least one processor, the so-called CPU (central processing unit). Furthermore, a mobile device particularly comprises means for cellular network connectivity for connecting to a mobile network, such as for example GSM (Global System for Mobile Communications), 3G, 4G or 5G, CDMA (Code Division Multiple Access), CDMA2000, UTMS (Universal Mobile Telecommunications System), or LTE (Long Term Evolution).

The mobile device comprises a display screen with a small numeric or alphanumeric keyboard or a touchscreen configured to provide a virtual keyboard and buttons (icons) on-screen. The mobile device is particularly configured to connect to the Internet and interconnect with other computerized devices via Wi-Fi, Bluetooth or near field communication (NFC). Integrated cameras, digital media players, mobile phone and GPS capabilities are common.

Further features and advantages of the invention shall be described by means of a detailed description of embodiments, wherein all the embodiments disclosed in the examples section can also be used in combination with the claimed subject matter.

Method for accurately estimating one or more pure tone audiometric thresholds from data collected in potentially sub-optimal test conditions The underlying problem is to be able to perform hearing tests under uncertain conditions. Traditional hearing tests can only be performed under very defined circumstances. This includes certain limits on background noise as well as knowing exactly the technical parameters of the hardware (headphones as well as audiometer/signal generator, how they interact). Therefore, hearing tests require a sound-proof environment while the hardware needs to undergo regular re-calibration. Due to constraints on cost and effort, both conditions can typically only be satisfied in professional settings. However, there is huge interest in performing hearing tests for screening or diagnosis with commodity hardware (such as smartphones) in less well sound-controlled environments. This enables a more regular and widespread testing in developed countries and opens up entirely new health care opportunities in countries where the hearing test infrastructure is limited or missing entirely. The present invention addresses this issue by offering a solution that circumvents the restrictions of classical hearing testing.

There is a well-known correlation between pure tone audiometry (the lowest intensity tones that a person can detect) and supra-threshold (tests conducted in the audible intensity range of the listener) measures of hearing. These are known through testing in a controlled environment. A controlled environment involves (a) calibration of hardware, (b) control of environmental noise so as not to mask test stimuli. Pure tone thresholds must be measured in a controlled environment to be meaningful, whereas supra-threshold measures need not necessarily be measured in a controlled environment. Supra-threshold stimuli are often presented in levels of dB SL (decibel sensation level), which is a sound level relative to the person's threshold. Threshold can be estimated on an arbitrary scale and calibration can be used to achieve a physically meaningful quantity, but the calibration step is not a requirement to present a stimulus at a known dB SL, i.e. the units are just a ratio. Furthermore, supra-threshold tests are by nature presented at higher stimulus intensities than the pure tone threshold, and are thus potentially more resilient to interference from background noise.

The method according to the invention involves using these facts to make predictions of the more basic standardised measure (pure tone audiogram, or more specifically one or more thresholds for broader protection) from one or more advanced measures (supra-threshold audiometrics). This invention facilitates:

Prediction of pure tone audiograms using data measured in uncontrolled environments.

Improvement or validation of the accuracy of pure tone audiograms measured in controlled environments, or estimated in uncontrolled environments.

Therefore the method according to the invention can be described as a combination of one or more types of supra-threshold audiometric tests, consisting of one or more repeated measures, to predict one or more pure tone thresholds for an individual.

Wherein particularly non-speech supra-threshold tests are used, and/or the STT is a PTC or TFS.

The method is carried out on a smartphone, mobile device or other personal computer as an audio-system.

The method is carried out in combination with one or more pure tone threshold measurements.

The method is carried out in combination with a pure tone audiogram measurement to further enhance the accuracy of the prediction.

The method is carried out in combination with a pure tone audiogram estimate to enhance the accuracy of the supra-threshold measures themselves in combination with the historic series of data sets.

The method is carried out in combination with information about the hardware used to collect the data.

The method is carried out in combination with data about the acoustic environment in which any diagnostics are performed.

The method is carried out in combination with data about the cognitive capacity of the patient at the time the diagnostics were performed.

The method is carried out in combination with the data from other patients (and particularly confirmed clinical-standard pure tone audiometry).

The method is carried out in combination with other available meta information about the data sets:
a) Reaction times
b) Estimated accuracy of data set
c) Time of day
d) Geographic location
e) Demographic user information (age, sex, etc.)
f) Test duration
g) Number of interruptions One example of an embodiment of the method according to the invention is given as follows:
At least one pure tone threshold particularly in arbitrary units on an unreferenced audio-system is determined or measured,
supra-threshold stimuli (i.e. sound signals) at defined sound level above threshold (decibel signal level) to measure a PTC are presented to a person,
a steepness of each of the downward and upward slopes defining the v-shaped curve or the width of the v-shaped PTC at a particular level above the minimum is estimated, determined or computed.
From that an individual absolute pure tone threshold according to the known general relationship between steepness/width of the v-shaped PTC and absolute pure tone thresholds is directly estimated.
For example, more generally:
Measure PTC curve for an individual user
Quantitatively parameterise the PTC curve according to a pre-determined scheme
Estimate pure tone threshold based on known general relationship between one or several of these parameters.

It is important to note that particularly only the shape of the PTC is needed to correlate against a database in order to estimate a pure tone threshold. Actual numbers on the y-axis are irrelevant. So, it is possible to estimate the threshold looking at the data alone, or, if there are more than one threshold from machine 1, we can use the supra-threshold data from machine 2, for one of those thresholds to maybe put units on both thresholds.

Further features and advantages of the invention shall be described by means of a detailed figure description, wherein features disclosed in the figure section can also be used in combination with the claimed subject matter.

FIG. 1 shows an illustration of a PTC measurement. A signal tone 102 is masked by a masker signal 105 particularly sweeping 103 through different frequencies in the proximity of the signal tone 102. The test person is indicating at which sound level he hears the signal tone for each masker signal. The signal tone and the masker signal are well within the hearing range of the person.

The diagram shows in the x-axis the frequency and on the y-axis the audio level or intensity in arbitrary units.

While a signal tone 102 that is constant in frequency and intensity 101 is played to the person a masker signal 105 slowly sweeps 103 from a frequency lower to a frequency higher than the signal tone 102. The rate of sweeping 103 is constant or can be controlled by the test person or the operator. The goal for the test person is to hear the signal tone 102. When the test person is not hearing the signal tone 102 anymore (which is for example indicated by the user by releasing a pushbutton) the masker signal is intensity is reduced 104 to a point where test person starts hearing the signal tone 102 (which is for example indicated by the user by pressing the push button). While the masker signal tone 105 is still sweeping 103 upwards in frequency, the intensity of the masker signal 105 is increased 104 again, until the test person does not hear the signal tone 102 anymore. This way, the masker signal intensity oscillates 106 around the hearing level 107 (as indicated by the solid line) of the test person with regard to the masker signal frequency and the signal tone.

This hearing level 107 is well established and well known for people having no hearing loss. Any deviations from this curve indicate a hearing loss (see for example FIG. 2).

Figure 2:
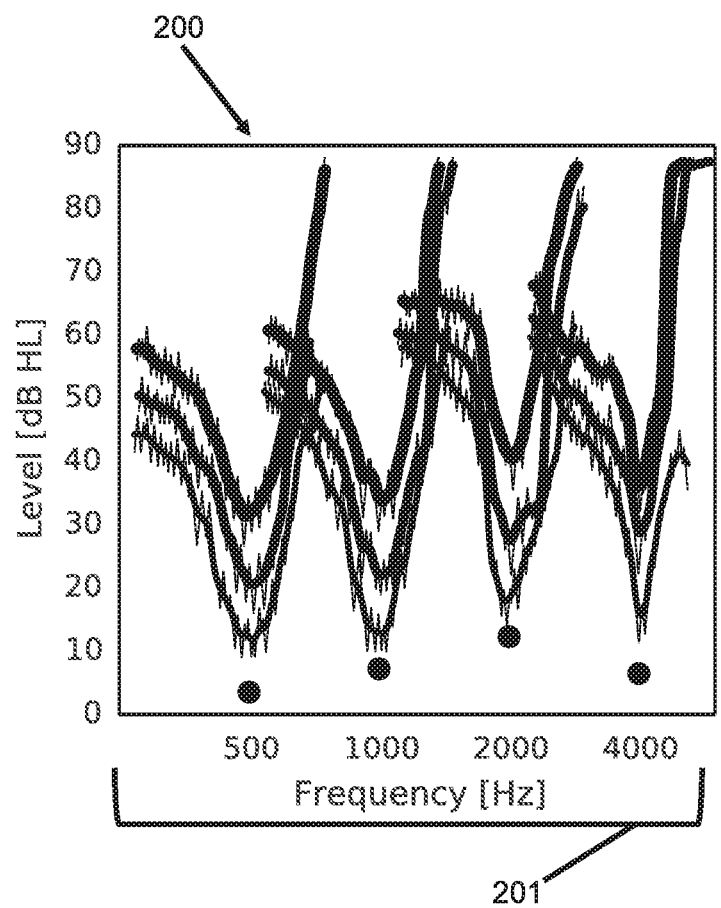
FIG. 2 shows the test results acquired on a calibrated setup in ordgLtogenerate a training set, according to one aspect of the present disclosure.
Figure 2:
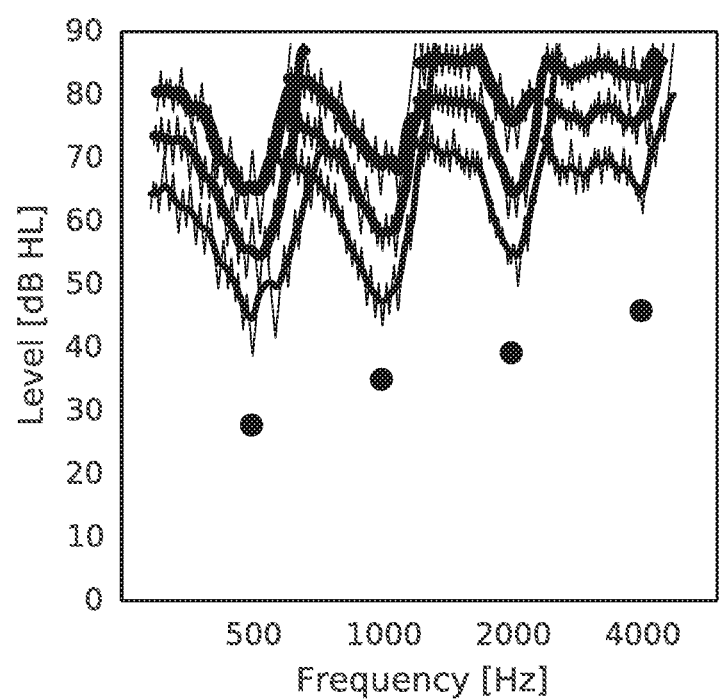

FIG. 2 shows the test results acquired on a calibrated setup in order to generate a training set for the method according to the invention. Therefore, the acquired PTC tests 200 can be given in absolute units such as dB HL. However, this is not crucial for the further evaluation.

In the present example, four PTC tests 200 at different signal tone frequencies 201 (500 Hz, 1 kHz, 2 kHz and 4 kHz) and at three different sound levels (40 dB HL, 30 dB HL and 20 dB HL; indicated by the thickness of the lines; the thicker the line the lower the signal tone level) for each signal tone have been performed. Therefore, at each signal tone frequency, there are three PTC curves. The PTC curves each are essentially v-shaped.

Dots below the PTC curves indicate the results from a calibrated—and thus absolute—pure tone threshold test performed with the same person.

On the upper panel, the PTC results and pure tone threshold test results acquired from a normal hearing person are shown, wherein on the lower panel, the same tests are shown for a hearing impaired person.

In the example shown, a training set comprising 20 persons, both normal hearing and hearing impaired persons, has been acquired.

Figure 3:
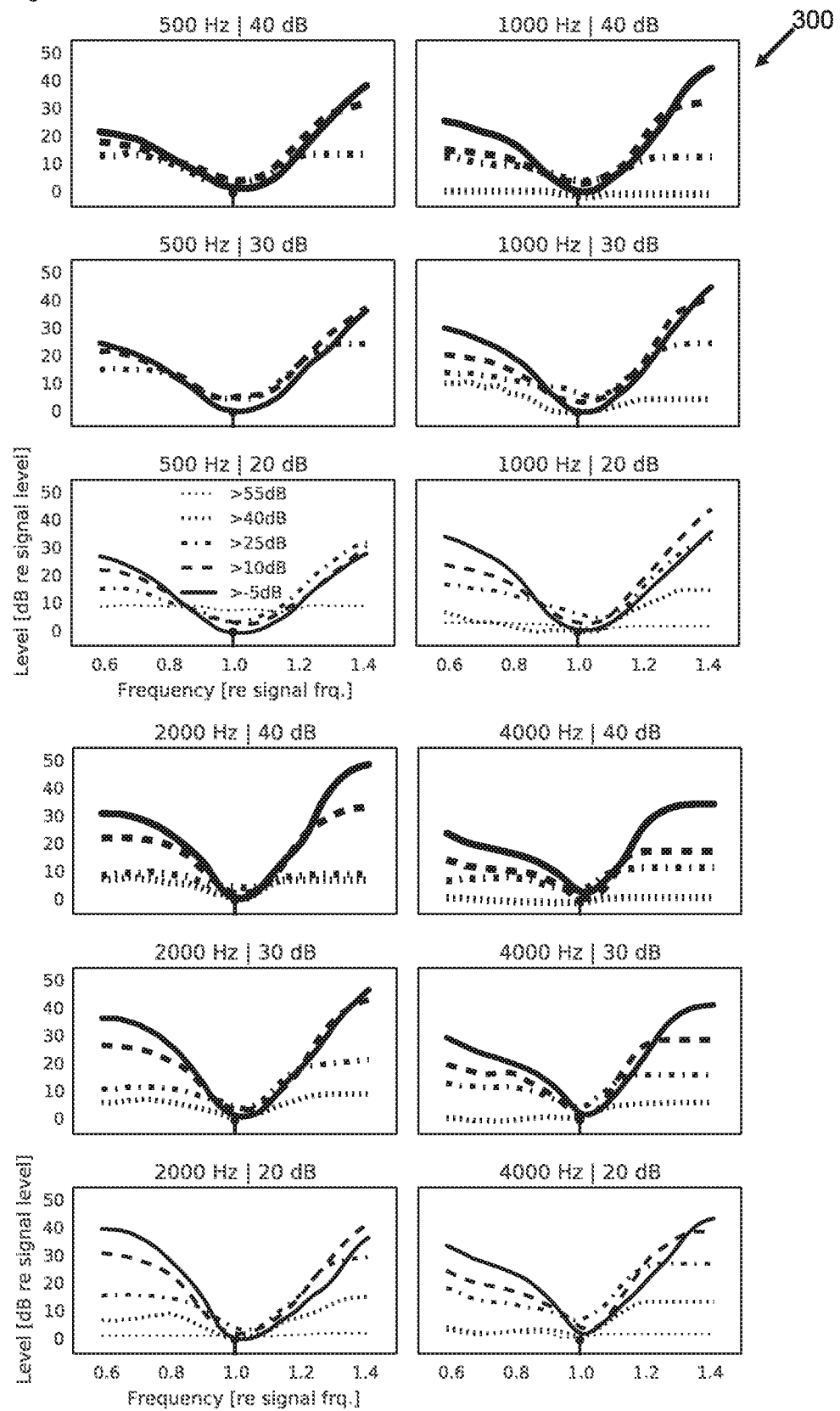
FIG. 3 a summary of the PTC test results of the training, according to one aspect of the present disclosure.

In FIG. 3 a summary of the PTC test results of the training set are shown 300. The plots are grouped according to single tone frequency and sound level resulting in 12 panels.

In each panel the PTC results are grouped in 5 groups (indicated by different line styles), according to their associated pure tone threshold test result. In some panels pure tone thresholds were not available, so these groups could not be established.

The groups comprise the following pure tone thresholds indicated by line colour: thin dotted line: >55dB, thick dotted line: >40 dB,: dash-dot line >25 dB, dashed line: >10 dB and continuous line: >−5 dB The PTC curves have been normalized relative to signal frequency and sound level for reasons of comparison. Therefore, the x-axis is normalized with respect of the signal tone frequency. The x-axes and y-axes of all plots show the same range.

As can easily be discerned across all graphs, elevations in threshold gradually coincide with wider PTCs, i.e. hearing impaired (HI) listeners have progressively broader tuning compared to normal hearing (NH) people.

This qualitative observation can be used for quantitatively determining at least one pure tone threshold from the shape-features of the PTC.

Modelling of the data is realised using a multivariate linear regression function of individual pure tone thresholds against corresponding PTCs across users, with separate models fit for each experimental condition (i.e. for each signal tone frequency and sound level).

Figure 4:
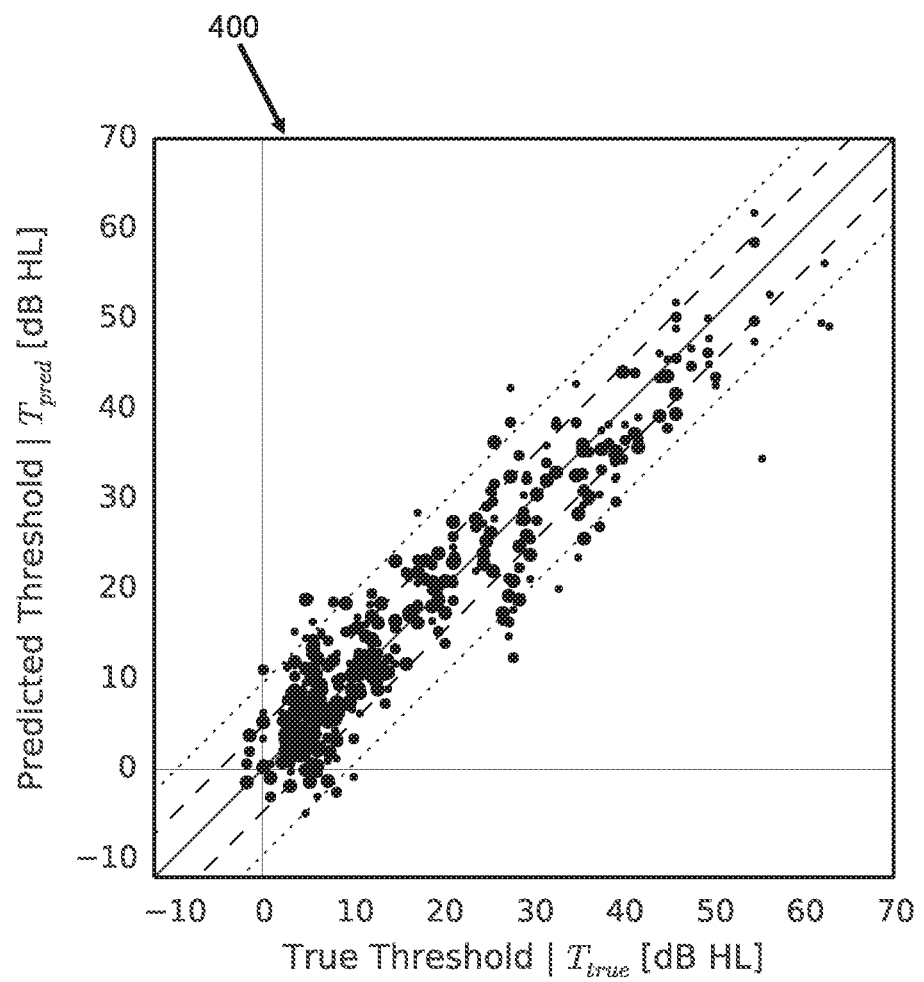
FIG. 4 shows the PTC-predicted vs. true audiometric pure tone thresholds, according to one aspect of the present disclosure.
Figure 5:
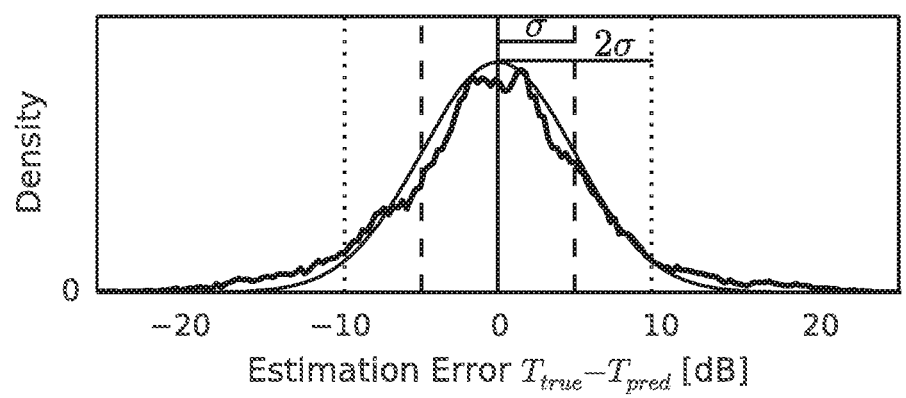
FIG. 5 shows a histogram of the differences between true and predicted pure tone thresholds, according to one aspect of the present disclosure.
Figure 6:
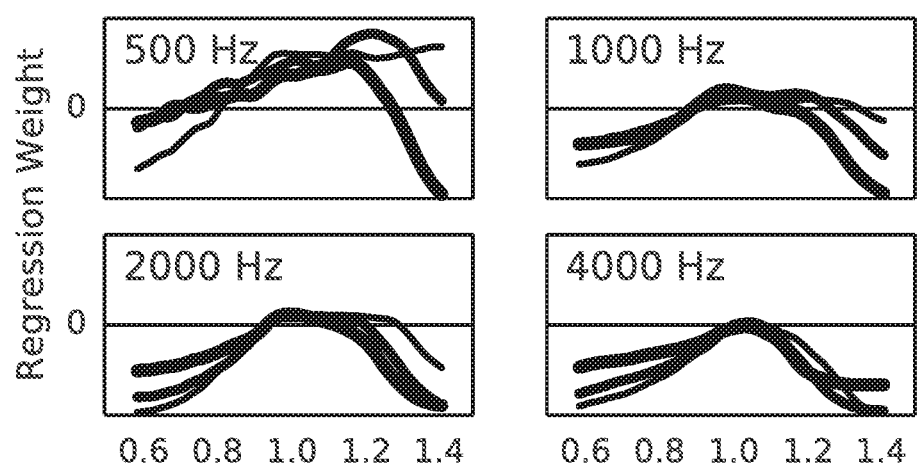
FIG. 6 shows regression weights of linear model across PTC signal frequencies (=subplots) and signal levels (=line thickness), according to one aspect of the present disclosure.

To capture the dominant variabilities of the PTCs across users and in turn reduce dimensionality of the predictors, i.e. to extract a characterizing parameter set PTC traces are subjected to a principle component analysis (PCA). Including more than the first five PCA components does not improve predictive power. FIGS. 4 and 5 summarise the fitted models' threshold predictions. Across all users and conditions, the standard absolute error of estimation amounted to 4.8 (1.7) dB, 89% of threshold estimates were within standard 10 dB variability. FIG. 6 plots regression weights across PTC masker frequency and indicates that mostly low-, but also high-frequency regions of a PTC trace are predictive of corresponding thresholds.

Thus, with the such generated regression function it is possible to determine an absolute pure tone threshold from an uncalibrated audio-system, as particularly the shape-feature of the PTC can be used to conclude form a PTC of unknown absolute sound level to the absolute pure tone threshold.

FIG. 4 shows the PTC-predicted 400 vs. true audiometric pure tone thresholds across all users and experimental conditions (marker size indicates the PTC signal level). Dashed (dotted) lines represent unit (double) standard error of estimate.

FIG. 5 shows a histogram of the differences between true and predicted pure tone thresholds, including an approximate normal distribution (smooth solid line).

FIG. 6 shows regression weights of linear model across PTC signal frequencies (=subplots) and signal levels (=line thickness) on a frequency normalized plot.

Figure 7:
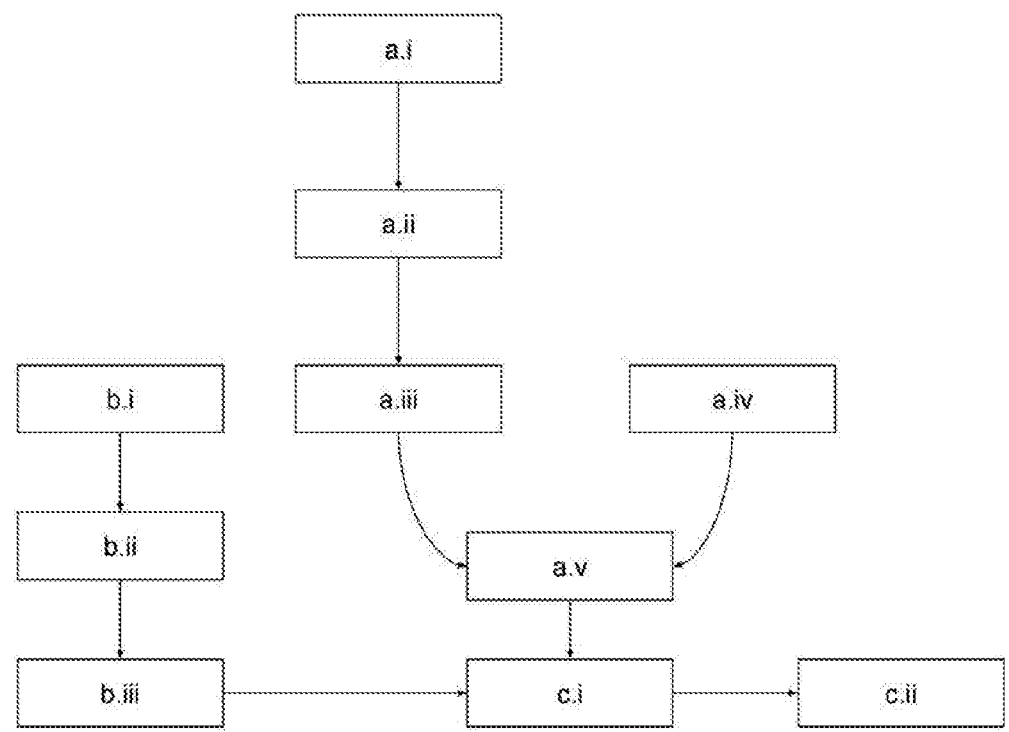
FIG. 7 shows a flow diagram of a method, according to one aspect of the present disclosure.

FIG. 7 shows a flow diagram of the method according to the invention. First, a training phase is initiated, where on a calibrated setup, PTC data are collected (step a.i).

In a.ii these data are pre-processed and then analysed for PTC features (step a.iii).

The training of the classifier (step a.v) takes the PTC features (also referred to as characterizing parameters) as well as related pure-tone thresholds (step a.iv) as input.

The actual prediction phase starts with step b.i, in which PTC data are collected on an uncalibrated setup. These data are pre-processed (step b.ii) and then analysed for PTC features (step b.iii).

The classifier (step c.i) using the setup it developed during the training phase (step a.v) predicts at least one pure-tone threshold (step c.ii) based on the PTC features of an uncalibrated setup.

The invention claimed is:

1. A method for estimating pure tone hearing thresholds or pure tone audiograms of a person from results of a supra-threshold test with an unreferenced audio-system on a mobile device, the method comprising:
performing, at the mobile device, a first supra-threshold test over at least over a portion of an audible frequency spectrum with a person, wherein the audible frequency spectrum ranges from 16 Hertz (Hz) to 20,000 Hz, wherein the first supra-threshold test is performed on the unreferenced audio-system at a first sound level relative to a predefined output level of the unreferenced audio-system;
determining, at the mobile device, a result of the first supra-threshold test for at least the portion of the audible frequency spectrum, wherein the result of the first supra-threshold test is provided relative to the predefined output level of the unreferenced audio-system;
determining, at the mobile device, from the result of the first supra-threshold test, at least one absolute pure tone threshold, wherein the at least one absolute pure tone threshold is provided in absolute physical units, including in decibels hearing level or in decibels sound pressure level.

2. The method according to claim 1, wherein the result of the first supra-threshold test comprises a characterizing parameter set, the characterizing parameter set including one or more of:
a parameter configured to describe one or more of a progression, a shape feature, a gradient or a shape of a graphical representation of the result of the first supra-threshold test; and
a set of principal components of the result of the first supra-threshold test, wherein the set of principal components comprises not more than 5 different principal components of the result of the first supra-threshold test.

3. The method according to claim 1, wherein the at least one absolute pure tone threshold is determined based at least in part by submitting one or more of the characterizing parameter set or the result of the first supra-threshold test to a regression function, wherein the regression function is configured to thereby determine the at least one pure tone threshold.

4. The method according to claim 3, wherein the regression function is determined by:
obtaining a training set comprising a plurality of estimated results of a reference supra-threshold test, the plurality of estimated results estimated from a plurality of people, wherein:
the reference supra-threshold test is the same as the first supra-threshold test; and
each estimated result of the plurality of estimated results of the reference supra-threshold test includes a corresponding estimated characterizing parameter set, each estimated result associated with at least one estimated absolute pure tone threshold;
performing a regression analysis of the training set in order to thereby determine the regression function, wherein the regression function is determined between the plurality of estimated results of the reference supra-threshold test and the at least one estimated absolute pure tone threshold associated with each one of the plurality of estimated results of the reference supra-threshold test.

5. The method according to claim 3, wherein:
the regression function is a multivariate linear regression function;
one or more variables of the regression function are selected from the estimated characterizing parameter sets of the plurality of estimated results of the reference supra-threshold test; and
one or more coefficients of the regression function are determined from the training set.

6. The method according to claim 1, wherein the at least one absolute pure tone threshold is determined by:
providing a database of a plurality of historical results of a reference supra-threshold test, wherein:
the reference supra-threshold test is the same as the first supra-threshold test;
the plurality of historical results are acquired from a plurality of persons; and
each one of the plurality of historical results has at least one associated absolute pure tone threshold;
analyzing, using a predefined similarity metric, at least a portion of the plurality of historical results of the reference suprathreshold test against the result of the first supra-threshold test, and determining a best-match historical result for the result of the first supra-threshold test based on the pre-defined similarity metric; and assigning the absolute pure tone threshold for the result of the first supra-threshold test such that the absolute pure tone threshold for the result of the first supra-threshold test is the same as the associated absolute pure tone threshold of the best-match historical result.

7. The method according to claim 1, wherein the first supra-threshold test comprises one or more of: a psychometric tuning curve test, a temporal fine structure test, and a temporal masking curve test.

8. The method according to claim 1, wherein performing the first supra-threshold test comprises performing a plurality of different supra-threshold tests on the unreferenced audio-system, wherein the plurality of different supra-threshold tests are performed at different sound levels or in different portions of the frequency spectrum.

9. The method according to claim 1, wherein the first supra-threshold test is a psychometric tuning curve test measured for a plurality of signal tones each having a corresponding signal tone frequency, the corresponding signal tone frequencies including 500 Hz, 1 kHz, 2 kHz and 4 kHz, wherein a masking signal of each one of the plurality of signal tones sweeps from 60% of the corresponding signal tone frequency to 140% of the corresponding signal tone frequency.

10. The method according to claim 1, wherein before the first supra-threshold test is performed, the method further comprises:

performing a pure tone threshold test with the unreferenced audio-system, wherein a sound level for each signal tone of the pure tone threshold test is referenced to the predefined output level of the unreferenced audio-system;

determining pure tone thresholds, wherein determining pure tone thresholds comprises determining a pure tone audiogram from the pure tone threshold test, wherein the pure tone thresholds are provided relative to the predefined output level of the unreferenced audio-system;

wherein the first sound level of the first supra-threshold test is higher by a predefined value than at least one of the pure tone thresholds provided relative to the predefined audio level; and wherein after the at least one absolute pure tone threshold is determined, the pure tone thresholds estimated before the first supra-threshold test are referenced against the at least one absolute pure tone threshold.

11. The method according to claim 10, wherein the predefined output level of the unreferenced audio-system is estimated by providing hardware information about the unreferenced audio-system, prior to the performance of either the first supra-threshold test or the pure tone threshold test.

12. The method according to claim 1, wherein:

a second supra-threshold test is performed with a second sound level relative to the predefined output level of the unreferenced audio-system; and the at least one absolute pure tone threshold is determined from a result of the second supra-threshold tests performed at the second sound level, using one or more of a regression function and a multivariate linear regression function.

13. The method according to claim 1, wherein:

the result of the first supra-threshold test is a function of at least one input frequency; and a progression of the result of the first supra-threshold test includes one or more of a shape, a slope or a specific feature of the function of the at least one input frequency, where the specific feature comprises one or more of a width of a locally v-shaped function, a width of a locally parabolic-shaped function, a local minimum, a steepness of a locally v-shaped function, and a steepness of a locally parabolic-shaped function.

14. The method according to claim 1, wherein a plurality of different supra-threshold tests are performed and, for each obtained result of each one of the plurality of different supra-threshold tests, a corresponding absolute pure tone threshold is determined.

* * * * *